United States Patent [19]

Tung et al.

[11] Patent Number: 5,545,778
[45] Date of Patent: Aug. 13, 1996

[54] SINGLE STAGE PROCESS FOR PRODUCING HYDROFLUOROCARBONS FROM PERCHLOROETHYLENE

[75] Inventors: Hsueh S. Tung, Getzville; Addison M. Smith, Amherst; Charles F. Swain, Williamsville, all of N.Y.

[73] Assignee: AlliedSignal Inc., Morris County, N.J.

[21] Appl. No.: 248,981

[22] Filed: May 25, 1994

[51] Int. Cl.$^6$ .......................... C07C 17/38; C07C 17/08
[52] U.S. Cl. .......................... 570/178; 570/165; 570/166; 570/167; 570/168; 570/169
[58] Field of Search .................. 570/178, 165, 570/166, 167, 168, 169

[56] References Cited

U.S. PATENT DOCUMENTS

| | | | |
|---|---|---|---|
| 2,478,362 | 8/1949 | Benning | 570/178 |
| 3,258,500 | 6/1966 | Swamer et al. | 260/653.7 |
| 4,766,260 | 8/1988 | Manzer et al. | 570/168 |
| 4,843,181 | 6/1989 | Gunprecht et al. | 570/169 |
| 4,911,792 | 3/1990 | Manzer et al. | 203/39 |
| 4,967,023 | 10/1990 | Carmello et al. | 570/166 |
| 5,091,601 | 2/1992 | Carmello et al. | 570/166 |
| 5,155,082 | 10/1992 | Tung et al. | 502/228 |

FOREIGN PATENT DOCUMENTS

| | | | |
|---|---|---|---|
| 0503771 | 9/1992 | European Pat. Off. | 570/178 |
| A0609123 | 8/1994 | European Pat. Off. | |
| A901297 | 7/1962 | United Kingdom | |
| WOA9216479 | 10/1992 | WIPO | |

*Primary Examiner*—Alan Siegel
*Attorney, Agent, or Firm*—Jay P. Friedenson

[57] ABSTRACT

A process for the preparation of one or more of $CHClFCF_3$ (HCFC-124), $CHF_2CClF_2$ (HCFC-124a) and $CHF_2CF_3$ (HFC-125) by reaction of perchloroethylene with hydrogen fluoride in a single stage reaction vessel in the presence of a fluorination catalyst. These compounds are useful in a variety of industrial applications including blowing agents, refrigerants, sterilant gases and solvent applications. Distilling the reaction product produces a distillate comprising HCl, $CHClFCF_3$, $CHF_2CClF_2$ and $CHF_2CF_3$ and a minor amount of HF which distillate is scrubbed to remove the acids. The bottoms product comprises perchloroethylene, hydrogen fluoride and organic by-products which is phase separated to sequester the hydrogen fluoride from the mixture of perchloroethylene and organic by-products. The hydrogen fluoride and mixture of perchloroethylene with organic by-products are then preferably re-mixed at a controlled rate and recycled to the reaction vessel.

20 Claims, 1 Drawing Sheet

SINGLE STAGE PROCESS FOR PRODUCING HYDROFLUOROCARBONS FROM PERCHLOROETHYLENE

FIELD OF THE INVENTION

The present invention pertains to a process for producing hydrochlorofluorocarbons and hydrofluorocarbons. In particular, the invention relates to the production of $CHClFCF_3$ (HCFC-124), $CHF_2CClF_2$ (HCFC-124a) and $CHF_2CF_3$ (HFC-125) from perchloroethylene in a single stage reactor. These compounds are useful in a variety of industrial applications including blowing agents, refrigerants, sterilant gases and solvent applications.

BACKGROUND OF THE INVENTION

Numerous chlorofluorocarbons (CFCs) are known in the art to have industrial and household applications including uses as refrigerants, solvents and blowing applications, however, they are believed to be deleterious to the earth's protective ozone layer. Because of the potential danger to atmospheric ozone by CFCs, it is desired to develop substitutes which function in substantially the same way but which are essentially not ozone depleting. Several such replacement materials include 1-chloro- 1,2,2,2-tetrafluoroethane (HCFC-124), 1-chloro-1,1,2,2,-tetrafluorochloroethane (HCFC-124a) and pentafluoroethane (HFC-125). It is expected that the demand for these materials will increase dramatically in the future and hence commercially viable processes for the preparation of these materials are advantageous. Many processes for the production of HCFC's and HFC's are known in the art. Many of these use catalysts which are not very selective and in addition to producing the desired materials, produce a wide variety of undesired by-products. Some of the catalysts have a very short life span and hence they are impractical for commercial application. In addition, the operating conditions described in the art made commercial production impractical. The following are typical of prior art methods.

U.S. Pat. No. 3,258,500 describes a single stage process for the production of HCFC-124 and HFC-125 by reacting tetrachloroethylene with anhydrous hydrogen fluoride in the presence of a fluorination catalyst. The catalyst may be activated anhydrous chromium oxide on alumina. This process has an exceedingly low selectivity and yield. U.S. Pat. No. 4,843,181 describes a gas phase single stage process which reacts tetrachloroethylene with hydrogen fluoride in the presence of chromium oxide. In order to obtain the desired product, an extremely long contact time is required between the catalyst and the reactants. U.S. Pat. No. 4,967,023 discloses a single stage process which hydrofluorinates perchloroethylene with a chromia on $AlF_3$ catalyst. A low conversion of reactants is noticed. Similar single stage processes and low yields are described in U.S. Pat. No. 4,766,260. The gas phase, single stage conversion of perchloroethylene to other HCFC's is shown in U.S. Pat. No. 5,091,601.

U.S. Pat. No. 5,155,082 describes a partially fluorinated aluminum/chromium oxide catalyst for the hydrofluorination of a halogenated aliphatic hydrocarbon to produce a chlorofluorocarbon, hydrochlorofluorocarbon or hydrofluorocarbon. According to this patent, when HCFC-124 is the desired hydrofluorocarbon the preferred starting material is HCFC-123 or HCFC-123a. HCFC-123 or HCFC-123a, in turn, preferably is produced from perchloroethylene as the starting material. This entails a two reactor system. Although it mentions that many of the by-products formed during the course of the fluorination reactions can be recycled for the production of additional hydrochlorofluorocarbons and HCFC-124 is specifically listed as one of the byproducts of the production of HCFC-123 from perchloroethylene, there is no disclosure of any process for obtaining HCFC-124, HCFC-124a or HFC-125 as the major products from perchloroethylene from a single step reaction. Prior to this invention the production of HCFC-124 involved two separate reactive stages. First perchloroethylene was hydrofluorinated to produce HCFC-123 and HCFC-123a and then in a separate reactive system, the HCFC-123 and HCFC-123a were hydrofluorinated to produce HCFC-124. Now, due to this invention, there is no longer a need for two separate reactive stages and all the additional equipment which such a two stage system would require. The process of the invention produces HCFC-124 as the major product, as well as HCFC-124a and HFC-125 from perchloroethylene in a single reactive stage. Consequently, one significant advantage is that less equipment is required, particularly since only one reactor vessel is necessary.

SUMMARY OF THE INVENTION

The invention provides a process for the preparation of one or more of $CHClFCF_3$, $CHF_2CClF_2$ and $CHF_2CF_3$ which comprises reacting perchloroethylene with hydrogen fluoride in a vapor phase in the presence of a fluorination catalyst in a reaction vessel. Thereafter the reaction product is distilled to thereby produce a distillate comprising HCl, $CHClFCF_3$, $CHF_2CClF_2$ and $CHF_2CF_3$ and a minor amount of HF, and a bottoms product comprising perchloroethylene, hydrogen fluoride and organic intermediates. A phase separation of the bottoms product is then carried out to thereby substantially separate the hydrogen fluoride from a mixture of perchloroethylene and organic intermediates.

DETAILED DESCRIPTION OF THE INVENTION

Figure 1:
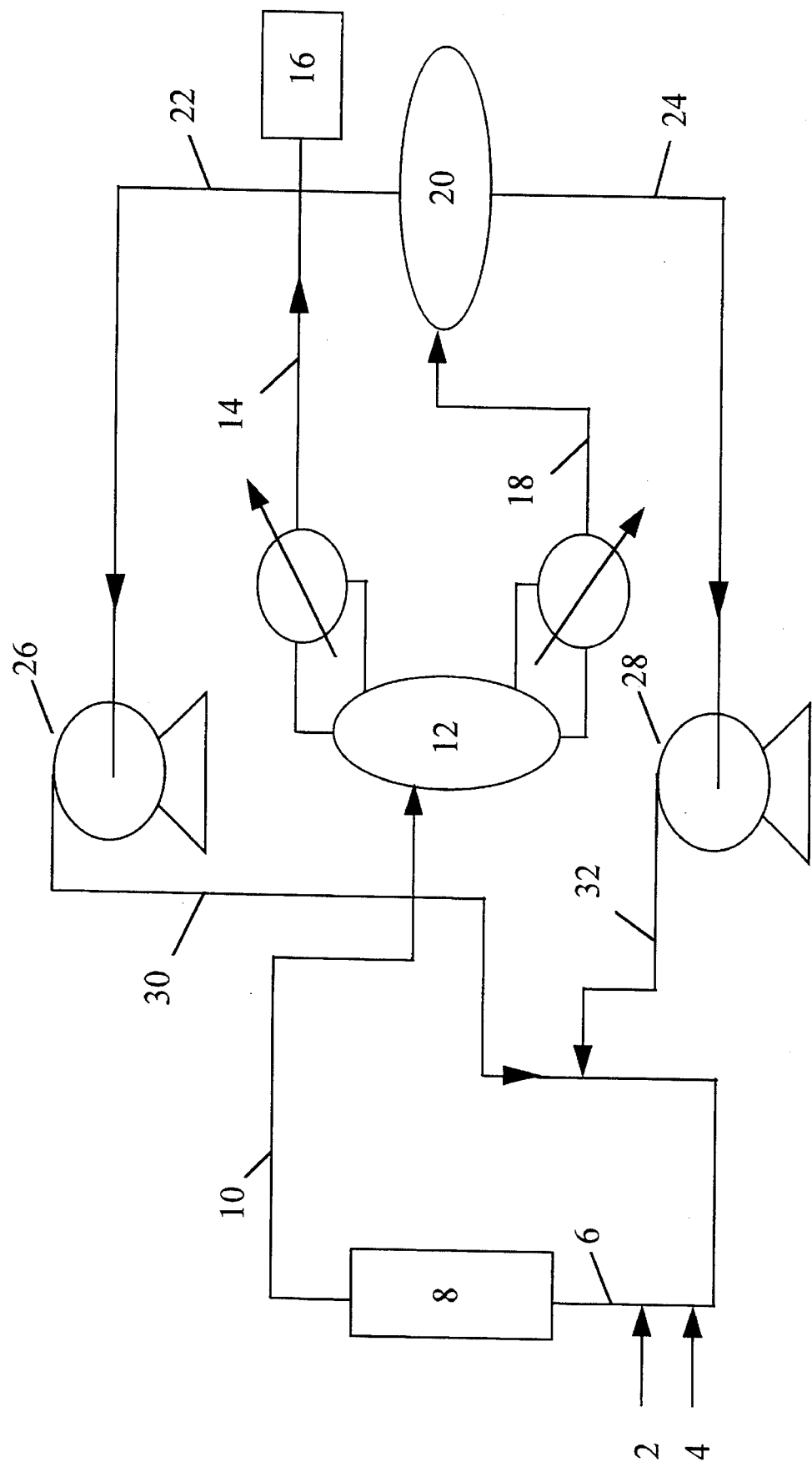
FIG. 1 shows a schematic representation of the process of the invention.

As a first step in the inventive process, perchloroethylene and anhydrous hydrogen fluoride are reacted together in the presence of catalyst. The reaction may be conducted in any suitable reaction vessel but it should be constructed from materials which are resistant to the corrosive effects of hydrogen fluoride such as HASTALLOY, INCONEL and MONEL. The mole ratio of hydrogen fluoride to perchloroethylene is adjusted to be from about 2:1 to about 50:1, and preferably from about 5:1 to about 40:1, and most preferably from about 6:1 to about 20:1. The temperature at which the reaction is conducted preferably ranges from about 200° C. to about 600° C., or more preferably from about 250° C. to about 500° C. and most preferably from about 300° C. to about 400° C. in the reactor. The reactor is preferably an adiabatic reactor filled with a fluorination catalyst. The organic vapor is allowed to contact the fluorination catalyst for from about 0.5 to about 120 seconds, more preferably from about 2 to about 90 seconds and most preferably from about 10 to about 60 seconds. For purposes of this invention, contact time is the time required for the gaseous reactants to pass through the catalyst bed assuming that the catalyst bed is 100% void. The reactive pressure preferably ranges from about atmospheric pressure to about 400 psig, preferably from about 50 to about 300 psig and most preferably from about 100 to about 250 psig. Any of the fluorination catalysts known in the art may be used. Such fluorination catalysts non-exclusively include chromium, aluminum, cobalt, manganese, nickel and iron oxides, halides, oxyhalides and inorganic salts, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$ and $NiCl_2/AlF_3$. Chromium oxide/aluminum oxide catalysts are described in U.S. Pat. No. 5,155,082 which is incorporated herein by reference. The chromium oxide may be crystalline chromium oxide or amorphous chromium oxide. Amorphous chromium oxide is preferred. Chromium oxide ($Cr_2O_3$) is a commercially available material which may be purchased in a variety of particle sizes. Chromium oxide may be purchased, for example, from Great Western Inorganics of Golden, Colo. and Mallinckrodt Specialty Chemicals Company, St. Louis, Miss. In the preferred embodiment, small amount of gaseous oxygen or air flows through the chromium oxide to maintain catalyst activity. The amount of air or oxygen supplied to the reactor is preferably from about 0.01 to about 30 mole percent of oxygen relative to the total organics fed to the reactor. A more preferred amount ranges from about 0.05 to about 20 mole percent and most preferably from about 0.1 to about 10 mole percent. The resulting product mixture includes HCFC-124, HCFC-124a, HCFC-125, as well as 1,1-dichloro-2,2,2-trifluoroethane (HCFC-123), 1,1,2-trichloro-2,2-difluoroethane (HCFC-122), trichlorofluoroethylene (HCFC-1111), hydrogen chloride and unreacted hydrogen fluoride and perchloroethylene.

The product mixture then is subjected to distillation to form a distillate portion and a bottoms portion. The primary purpose of the distillation is to separate HCFC-124 from the hydrogen fluoride. Distillation, rather than another type of separation, is necessary for this separation because it was found that HCFC-124 dissolves in hydrogen fluoride. The distillation is preferably conducted at a pressure which ranges from about 5 psig to about 500 psig, preferably from about 10 to about 400 psig and most preferably from about 50 to about 300 psig. The pressure of the distillation column inherently determines the distillation operating temperature. The distillate portion includes substantially all the HCFC-124, HCFC-124a, HCFC-125, hydrogen chloride and air or oxygen present in the product mixture as well as a minor amount of hydrogen fluoride. The bottoms portion includes substantially all the hydrogen fluoride, perchloroethylene, HCFC-123, HCFC-122 and HCFC-1111 present in the product mixture. Optionally, an additional distillation column can be used prior to the above described distillation column to remove HCl and non-condensables such as air or oxygen.

In the preferred embodiment, the hydrogen chloride and hydrogen fluoride are then substantially removed from the distillate portion via a conventional scrubber leaving HCFC-124, HCFC-124a and HCFC-125. If desired, the HCFC-124, HCFC-124a and HCFC-125 can be individually separated via a conventional distillation process which is well known to the skilled artisan.

The bottoms portion is subjected to a phase separation wherein the hydrogen fluoride is separated from an organic portion which includes the perchloroethylene, HCFC-123, HCFC-122 and HCFC-1111. The phase separator can be a holding tank wherein the HF migrates to the top and the other ingredients settle to the bottom. The HF and bottom components are then individually pumped away. The hydrogen fluoride and the organic portion then are recycled so that they react with fresh hydrogen fluoride and perchloroethylene. Although both effluent streams are recycled back to the reactor, the phase separator is necessary to control the mole ratio of the reacting materials and to determine how much fresh feed needs to be added. A critical feature of the invention is that a reverse positioning of the phase separator before the distillation column will not produce a functioning process. This because HCFC-124 is soluble in hydrogen fluoride. They can be separated in the distillation column but not in the phase separator. Therefore, if the reverse order were used, the HCFC-124 would remain dissolved in the hydrogen fluoride. If a higher proportion of HCFC-125 is desired as the principal product, the distillation column can be operated at a lower condenser temperature in order to cause the HCFC-124 and HCFC-124a to exit by via the bottoms effluent for recycling and return to the reactor. Alternatively, the HCFC-124 and HCFC-124a can be returned for recycling and return to the reactor after exiting the scrubber.

FIG. 1 provides a schematic representation of a preferred process flow of the invention. A fresh gaseous hydrogen fluoride feed stream 2 and a fresh gaseous perchloroethylene feed stream 4 are mixed to form a reactor feed stream 6 which is fed into a reactor 8. The effluent from the reactor 10 is the product mixture stream which enters a distillation column 12. The distillate stream 14, includes HCFC-124 as the major product and additionally includes HCFC-124a, HFC-125, HCl, air or oxygen, and a minor amount of HF. In the preferred embodiment, distillate stream 14 is fed into additional separation and/or purification apparatus, such as a conventional scrubber 16 to remove the HF and HCl. Another distillation column (not shown), separates the component HCFC-124, HCFC-124a and HCFC-125. Such a scrubber is well known in the art and conventionally comprises a caustic scrubbing with aqueous NaOH or KOH under conditions sufficient to neutralize residual acidity.

The bottoms stream 18 is fed to a phase separator 20. This stream contains the vast majority of the hydrogen fluoride as well as an organic mixture of HCFC-123, HCFC-122, HCFC-1111 and perchloroethylene. Stream 18 is split by phase separator 20 into a first recycle stream 22 of HF and a second recycle stream 24 containing HCFC-123, HCFC-122, HCFC-1111 and perchloroethylene. Both of the recycle streams 22 and 24 are passed through pumps 26 and 28. The recycle streams 30 and 32 then merge into the reactor feed stream 6.

It will be readily appreciated that the respective amounts of the components of the product mixture will vary depending upon reactive conditions and catalysts employed. Similarly, the amounts of the components of the distillate and the bottoms portions may be varied by the skilled artisan.

The process of the invention provides a method for obtaining HCFC-124 as the major product at high productivity, normally greater than 10 lbs/hr/ft$^3$. As used herein, the term "major product" means the single product that is produced by the reactive system in the greatest amount. The present invention is more fully illustrated by the following non-limiting examples.

EXAMPLE 1

Substantially pure perchloroethylene (PCE) is fed into a 1 inch reactor made from MONEL at a rate of 60 g/hr. The reactor contains 110 ml of an amorphous $Cr_2O_3$ catalyst. The catalyst time on stream is 118 hours. The reactor temperature is 330° C. and the pressure is 50 psig. Anhydrous hydrogen fluoride (HF) is simultaneously fed to the reactor at the rate of 58.2 g/hr. The mole ratio of HF to PCE is 8. Air is co-fed to the reactor at an $O_2$:PCE mole ratio of about 2 mole %. The contact time is 11 seconds. The effluent of the reactor is analyzed using an on-line gas chromatograph. The results are shown in Table 1. PCE conversion is 67.1%. The combined 120's is about 96%. The HCFC-124/HFC-125 ratio was 3/1. The productivity of HCFC-124 and HCFC-124a is 5.6 lbs/hr/ft$^3$ catalyst. The total non-recyclable products were 3.8%. The major product is HCFC-123 and HCFC-123a, which is an intermediate for producing HCFC-124.

TABLE 1

| Selectivity (%): | |
| --- | --- |
| HFC-125 | 10.5 |
| HCFC-124 | 28.1 |
| HCFC-124a | 1.4 |
| HCFC-123 | 43.0 |
| HCFC-123a | 3.3 |
| HCFC-122 | 5.1 |
| HCFC-121 | 0.1 |
| HCFC-1111 | 4.8 |
| COMBINED 120's | 96.3 |
| Non-recyclable products: | |
| HCFC-133a | 0.7 |
| HCFC 1112 or HCFC-1112a | 0 |
| CFC-110's | 3.1 |
| Productivity (lbs/hr/ft$^3$) | |
| HCFC-123 and 123a | 9.8 |
| HCFC-124 and 124a | 5.6 |

EXAMPLE 2

In order to simulate the recycle of the intermediate HCFC-123, an organic feed of 30/70 weight % of PCE/HCFC-123 is fed to the same reactor used in Example 1. The pressure is 200 psig and HF and organics are also fed to the reactor at a HF:organic mole ratio of 7.6. The temperature is 330° C. The contact time is 18 seconds and the catalyst on stream time is 282 hours. Air is co-fed at a 1 mole % $O_2$:organics. The effluent of the reactor is analyzed using a gas chromatograph. The results are shown in the first column of Table 2. The productivity of HCFC-124 and HCFC-124a is increased to 11.5 lbs/hr/ft$^3$ catalyst. The combined 120's is 97.8%. The term "combined 120s" refers to the combined selectivities of the desired products and recyclable by-products of chlorofluorocarbons and/or hydrochlorofluorocarbons produced in a given hydrofluorination reaction. The HCFC-124/HFC-125 ratio is 1/0.08. The PCE conversion is 81.6%. The net conversion HCFC-123/HCFC-123a is 3.7, suggesting that HCFC-123 recycle ratio is about 70%. The total non-recyclable by-products is about 2.4%.

EXAMPLE 3

The same reactor and reaction conditions as in Example 2 are used, except the HF:organic mole ratio is changed to 4.9, the contact time is 24 seconds and the catalyst on stream time is 337 hours. The results are shown in the second column of Table 2. The change of the HF:organic mole ratio reduces 120's selectivity to 94.9% and increases the conversion of HCFC-123/HCFC-123a to 19.7. The PCE conversion is 78.1%. These results suggest that a lower HF:organic mole ratio is not beneficial to the reaction and reaction of PCE with HF appears to be slower than that of HCFC-123 and HF.

EXAMPLE 4

The same reactor and reactor conditions as in Example 3 are used, except that a lower pressure (100 psig) is used, the contact time is 13 seconds and the catalyst on stream time is 354 hours. The results are listed in the third column of Table 2. The PCE conversion was reduced to 67.8 as the pressure decreases, although the HCFC-123/HCFC-123a conversion increases to 31.0. These results suggest that high pressure is preferred for the single step process.

TABLE 2

| | EXAMPLE 2 | EXAMPLE 3 | EXAMPLE 4 |
| --- | --- | --- | --- |
| Selectivity (%): | | | |
| HFC-125 | 5.8 | 8.9 | 15.8 |
| HCFC-124 | 73.9 | 76.0 | 73.7 |
| HCFC-124a | 1.5 | 1.4 | 1.0 |
| HCFC-122/ HCFC-122a | 13.9 | 6.6 | 3.8 |
| HCFC-121 | 0.2 | 0.1 | 0.2 |
| HCFC-1111 | 2.5 | 1.9 | 2.0 |
| COMBINED 120's | 97.8 | 94.9 | 96.5 |
| Non-recyclable products: | | | |
| HCFC-133a | 0 | 0.1 | 0.1 |
| HCFC 1112 or HCFC-1112a | 0 | 0.01 | 0 |
| CFC-110's | 2.4 | 5.0 | 3.4 |
| Productivity (lbs/hr/ft$^3$) | | | |
| HCFC-124 and 124a | 11.5 | 16.2 | 18.1 |
| HCFC-125 | 0.78 | 1.6 | 3.4 |

What is claimed is:

1. A process for the preparation of one or more of $CHClFCF_3$, $CHF_2CClF_2$ and $CHF_2CF_3$ which comprises reacting perchloroethylene with hydrogen fluoride in a vapor phase in the presence of a fluorination catalyst in a reaction vessel; and then distilling the reaction product to thereby produce a distillate comprising HCl, $CHClFCF_3$, $CHF_2CClF_2$ and $CHF_2CF_3$ and a minor amount of HF, and a bottoms product comprising perchloroethylene, hydrogen fluoride and organic by-products; and then carrying out a phase separation of the bottoms product to thereby substantially separate the hydrogen fluoride from a mixture of perchloroethylene and organic by-products.

2. The process of claim 1 further comprising the subsequent step of treating the distillate to separate the $CHClFCF_3$, $CHF_2CClF_2$ and $CHF_2CF_3$ from the HCl and HF.

3. The process of claim 2 wherein the treating is conducted with a scrubber.

4. The process of claim 2 wherein the scrubber comprises aqueous NaOH or KOH.

5. The process of claim 2 further comprising the subsequent step of separating each of $CHClFCF_3$, $CHF_2CClF_2$ and $CHF_2CF_3$ by distillation.

6. The process of claim 5 further comprising the subsequent step of recycling the $CHClFCF_3$ and $CHF_2CClF_2$ as feed to the reaction vessel and wherein the product of the reaction comprises a major amount of $CHF_2CF_3$.

7. The process of claim 1 wherein the hydrogen fluoride and the mixture of perchloroethylene and organic by-products resulting from the phase separation are separately recycled as feed to the reaction vessel.

8. The process of claim 7 wherein the organic by-product portion of the bottoms product comprises one or more of $CHClFCF_3$ and $CHF_2CClF_2$ and wherein the product of the reaction comprises a major amount of $CHF_2CF_3$.

9. The process of claim 1 wherein a flow of oxygen or air is conducted to the catalyst during the reaction.

10. The process of claim 9 wherein the oxygen or air supplied in an amount of from about 0.01 to about 30 mole percent of $O_2$ based on the amount of perchloroethylene reacted.

11. The process of claim 1 wherein the fluorination catalyst is selected from the group consisting of chromium, aluminum, cobalt, manganese, nickel and iron oxides, halides, oxyhalides and inorganic salts, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$ and $NiCl_2/AlF_3$.

12. The process of claim 1 wherein the reaction is conducted at a temperature of from about 200° C. to about 600° C.

13. The process of claim 1 wherein the reaction is conducted at a pressures of from about atmospheric pressure to about 400 psig.

14. The process of claim 1 wherein the reactants contact the fluorination catalyst for a contact time of from about 0.5 seconds to about 120 seconds.

15. The process of claim 1 wherein the mole ratio of hydrogen fluoride to perchloroethylene ranges from about 4:1 to about 50:1.

16. The process of claim 1 wherein the total yield of $CHClFCF_3$, $CHF_2CClF_2$ and $CHF_2CF_3$ ranges from about 90% to about 98%.

17. The process of claim 1 wherein the total yield of $CHClFCF_3$ ranges from about 90% to about 98%.

18. The process of claim 1 wherein the distillation is conducted at a pressure which ranges from about 5 psig to about 500 psig.

19. The process of claim 1 wherein the reaction is conducted at a temperature of from about 300° C. to about 400° C., and at a pressures of from 100 psig to about 250 psig; the reactants contact the fluorination catalyst for a contact time of from about 10 seconds to about 60 seconds; the mole ratio of hydrogen fluoride to perchloroethylene ranges from about 6:1 to about 20:1; wherein a flow of oxygen or air is conducted to the catalyst during the reaction in an amount of from about 0.01 to about 30 mole percent of $O_2$ based on the amount of perchloroethylene reacted; the distillation is conducted at a pressure which ranges from about 50 to about 300 psig; and wherein the fluorination catalyst is selected from the group consisting of chromium, aluminum, cobalt, manganese, nickel and iron oxides, halides, oxyhalides and inorganic salts, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$ and $NiCl_2/AlF_3$.

20. The process of claim 1 wherein the hydrogen fluoride and the mixture of perchloroethylene and organic by-products resulting from the phase separation are separately recycled as feed to the reaction vessel.

* * * * *